United States Patent [19]

Sugisawa et al.

[11] Patent Number: 4,597,945
[45] Date of Patent: Jul. 1, 1986

[54] STERILIZATION APPARATUS

[75] Inventors: Ko Sugisawa; Kazuya Sekiguchi; Kiyoaki Tsuzi; Akinobu Ono, all of Higashiosaka, Japan

[73] Assignee: House Food Industrial Company Limited, Osaka, Japan

[21] Appl. No.: 587,368

[22] Filed: Mar. 8, 1984

[30] Foreign Application Priority Data

| Mar. 9, 1983 [JP] | Japan | 58-39705 |
| Mar. 18, 1983 [JP] | Japan | 58-46887 |
| Mar. 28, 1983 [JP] | Japan | 58-54916 |
| Sep. 29, 1983 [JP] | Japan | 58-183469 |

[51] Int. Cl.⁴ .......................... G05D 16/00
[52] U.S. Cl. ................... 422/113; 422/295; 141/44; 141/82
[58] Field of Search .............. 422/4, 26-28, 422/39, 40, 110, 111, 112, 113, 295, 297; 53/128; 141/82, DIG. 2, 37, 44

[56] References Cited

U.S. PATENT DOCUMENTS

| 1,364,803 | 1/1921 | Rankin | 422/113 |
| 2,160,062 | 5/1939 | Drake et al. | 422/295 |
| 3,529,625 | 9/1970 | Ferrari | 422/113 |
| 3,891,779 | 6/1975 | Robinson | 422/28 |
| 4,092,111 | 5/1978 | Gaignoux et al. | 422/198 |
| 4,452,030 | 6/1984 | Inada | 53/426 |

OTHER PUBLICATIONS

Die Molkerei Zeitung Welt der Milch, 35, Jahrgang, 1981/41, pp. 1300-1305.

Primary Examiner—David L. Lacey
Assistant Examiner—Titus B. Ledbetter, Jr.
Attorney, Agent, or Firm—Harry M. Weiss & Associates

[57] ABSTRACT

A sterilization apparatus suitable for sterilizing food and medicines containing solid particles, which comprises a forcing device, a sterilizer, a backpressure tank and a backpressure device. The sterilization apparatus is sterilized beforehand under application of a backpressure by employing the forcing device and the backpressure device. The products are sterilized in the sterilizer under pressure by the forcing device and the backpressure tank, and then the sterilized products are collected in the backpressure tank.

11 Claims, 5 Drawing Figures

STERILIZATION APPARATUS

BACKGROUND OF THE INVENTION

This invention relates to a sterilization apparatus suitable for the sterilizing treatment of liquids or pastes of food and medicines containing solid particles, and particularly to a sterilizing apparatus capable of collecting the products alone under a stable pressure to the inside of the apparatus and continuously discharging hot water during sterilization of the apparatus, water during operation with water, and a mixture of water and the products during change-over operation while maintaining the sterility of the product passages.

It is widely known that putrefaction occurring during storage of food and medicines is generally caused by microorganisms. In order to eliminate putrefaction of food and medicines, techniques for increasing the preservability of food and medicines by processing them with a bacteriological stable condition have been developed. One of the typical techniques is sterilization by heating of packed products as seen in canned and retort foods. In this technique, however, the inside of the containers has to be heated for a long period of time so as to kill the bacteria. A great problem of this technique, particularly in connection with food and medicines, is that heating for a long period of time impairs taste, efficacy and nutritional value and breaks down tissue.

It is preferred to carry out heating for a short time at a high temperature in sterilization of food and medicines. Recently, a method and an apparatus for sterilizing products at a high temperature in a short time before placing them into a container has attracted much attention along with aseptic packaging for packing of sterilized products in a contained under aseptic conditions.

Sterilization of food and medicines is usually carried out at a high temperature over 100° C., and boiling of the products occurs in the sterilizer at atmospheric pressure. Therefore, sterilization by heating must be carried out in the sterilizer under a pressure (termed as the backpressure hereinafter) so as to prevent boiling. In this respect, the conventional method and apparatus involved various problems.

More specifically, the conventional apparatus is provided with a feed pump for feeding the products into the sterilizer and a pump for sending the sterilized products to the next process, on the inlet and outlet ends of the sterilizer. A backpressure is applied to the sterilizer by control of the discharge rate of the pumps.

However, pulsation of or leakage from the pumps brings about fluctuations in the flow rate of the product passing through the sterilizer. This causes a change in backpressure applied to the sterilizer. Thus, the conventional apparatus has drawbacks in its pump functions. In the conventional apparatus, therefore, it was difficult to supply a stable backpressure to the sterilizer, and to sterilize the products under stable conditions.

In addition, it is difficult in the conventional apparatus to control accurately the backpressure to a desired value.

Furthermore, if the sterilization conditions are established so as to make the product aseptic, a very high temperature and a high pressure must be supplied to the rear pump. It is, therefore, difficult to sterilize the product under constant conditions from the viewpoint of the above pump functions. This is a fatal problem in an aseptic packaging apparatus. Also, if a rear pump is used which can endure a high temperature and high pressure, while maintaining aseptic conditions, the pump must be made of special materials and with a special design. In addition, it is difficult to obtain a stable flow rate in the low and high temperature zones in the apparatus.

If the product contains solid particles, most of the solid particles are broken up according to the above method, since the product passes twice through the pumps.

If the rear pump is replaced by a pressure relief valve or a homogenizer in the above method, it is possible to apply a fairly constant backpressure to inside apparatus. However, if the product contains solid particles or is highly viscous, accumulation of particles and blockage occurs at the pressure relief valve or the homogenizer, and causes troubles such as destruction of the apparatus due to an abnormal increase in pressure inside the apparatus. Therefore, the homogenizer or the pressure relief valve cannot be used in treating such products.

A sterilization apparatus suitable for sterilizing materials containing solid particles was described in a generally circulated West German magazine (Die Molkereizeitung Welt der Milch, 35. Jahrgang, 1981/41). This apparatus, which solves the above problems, is equipped with a feed pump in front of the sterilizer and a backpressure tank behind the sterilizer. In the sterilization apparatus, the backpressure tank is capable of controlling the air pressure, and a backpressure is supplied to the sterilizer by use of the air pressure in the backpressure tank. Therefore, even if the product contains solid particles, it is possible to treat it under constant high temperature conditions and stable application of a backpressure to the steilizer. Also, no clogging of solid particles occurs in the apparatus.

The sterilizing apparatus described in the magazine shows an excellent effect in sterilizing products containing solid particles as described above. However, the magazine refers only to the basic structure of an apparatus comprising a feed pump, a sterilizer and a backpressure tank, and clarifies the principle of applying a backpressure to the sterilizer by the air pressure.

In actual operation of the sterilizing apparatus, sterilization of the apparatus to secure the sterility of the whole apparatus before starting operation, operation with water, and change-over operation from water to products are required before operation with the product. Therefore, the sterilization apparatus must be equipped with mechanisms corresponding to each such step.

A conventional apparatus for sterilizing milk, or other products comprises, for example, a sterilizer, pumps before and behind the sterilizer, a device for recovering the milk or product provided behind the rear pump, and a device for discharging treated materials other than the milk or product. In the above apparatus, a backpressure is supplied to the sterilizer by means of the pumps, and all materials including hot water used for sterilizing the apparatus, water, a mixture of water and milk or the product, and the sterilized milk or product pass through the pump behind the sterilizer, and are then discharged or recovered.

In the apparatus for sterilizing milk, it is possible to carry out the operation from sterilization of apparatus to operation with the product by passing the product through the pump behind the sterilizer without installation of independent piping, etc. This is because the physical properties of hot water used for sterilization of the apparatus are similar to those of milk, and milk contains no solid particles.

However, if products containing solid particles are treated, it is impossible to satisfactorily carry out all processes from sterlization of the apparatus to recovery of the products in such an apparatus in which the rear pump in the above apparatus is replaced by a backpressure tank, i.e., an apparatus according to prior art as described above.

If materials containing solid particles are treated in the conventional apparatus, all of the hot water used for sterilization of the apparatus, the water used during operation with water, the mixture of water and the product used during change-over operation and the product are sent into the backpressure tank. Therefore, it is difficult to collect the products alone in a continuous operation from sterilization of the apparatus to operation with products under a backpressure.

Thus, in order to satisfactorily sterilize products containing solid substances the sterilization apparatus should have a structure capable of continuously discharging the treated materials other than the product and collecting the products alone under a stable backpressure to the inside of the apparatus while maintaining the sterile condition of the product passages.

SUMMARY OF THE INVENTION

An object of the invention is to provide a sterilization apparatus having the above functions which is suitable for continuously treating products containing solid particles.

The inventors have made investigations so as to achieve the above object. As a result, the inventors found that a constant backpressure may always be supplied to the inside of the apparatus and that the treated materials other than the products are continuously discharged out of the apparatus and the products alone can be collected in the backpressure tank while maintaining the sterile condition of the product passages by use of a sterilization apparatus comprising a sterilizer, a forcing device for forcing the product into the sterilizer, a backpressure tank capable of controlling the air pressure which is provided to the rear of the sterilizer, and a backpressure device for applying a backpressure to the sterilizer, the backpressure means being capable of passing solid particles, the backpressure tank being connected to said sterilizer by means of a feed pipe and said backpressure means being provided in an auxiliary backpressure pipe branching from said feed pipe. According to this apparatus: (1) hot water during sterilization of the apparatus, water during operation with water,and a mixture of water and the product during change-over operation are continuously discharged from the sterilizer through the auxiliary backpressure pipe, and at the same time, a backpressure is supplied to the inside of the apparatus by the backpressure means; (2) if the materials are completely changed over to the product, the product is continuously sent from the sterilizer to the backpressure tank for collection through the feed pipe, and at the same time, a backpressure is supplied to inside the apparatus by use of the air pressure in the backpressure tank; and (3) even if the product contains solid substances, a constant backpressure may always be supplied to inside the apparatus as in items (1) and (2).

The materials other than the product are continuously discharged outside the apparatus. On the other hand, only the product can be collected in the backpressure tank while maintaining the sterility of the product passages.

The inventors also found that the change-over operation to the product may safely be carried out without impairing the sterility of the backpressure tank by use of the sterilization apparatus of the above structure wherein the pressure inside the backpressure tank is controlled at a level higher than that supplied by the backpressure device during the change-over operation so as to eliminate a contrary flow of the materials from the auxiliary backpressure pipe to the backpressure tank.

The invention provides a sterilization apparatus for continuously sterilizing materials to be treated containing solid particles while keeping a pressure of the apparatus unchangeable comprising:

(1) a sterilizer being capable of passing said solid particles, (2) a feeding device for feeding said materials to said sterilizer, (3) a backpressure tank being capable of controlling the air pressure for supplying a backpressure to said sterilizer, (4) a backpressure device being capable of passing said solid particles and supplying a backpressure to said sterilizer, (5) a feed pipe for connecting said sterilizer with said backpressure tank, and (6) an auxiliary backpressure pipe branching from said feed pipe.

The invention also provides a sterilization apparatus comprising at least a sterilizer, a feeding device for feeding materials into said sterilizer, an aseptic tank capable of controlling the air pressure which is provided to the rear of said sterilizer, an auxiliary backpressure tank, a pressure relief valve for drainage and a drawing pump for drawing the materials from said auxiliary backpressure tank, said aseptic tank being connected to said sterilizer by means of a feed pipe, said auxiliary backpressure tank and said discharging pump being provided in an auxiliary backpressure pipe branching from said feed pipe, said pressure relief valve being provided in a discharge pipe branching from said feed pipe or said auxiliary backpressure pipe, and a backpressure being supplied to said sterilizer by means of said feeding device and one of said sterile tank, said auxiliary backpressure means and said pressure relief valve.

Furthermore, the invention provides a sterilization apparatus comprising at least a sterilizer, a feeding device for feeding materials into said sterilizer, an aseptic tank capable of controlling the air pressure which is provided to the rear of said sterilizer, a backpressure pump and a pressure relief valve for discharge, said aseptic tank being connected to said sterilizer by means of a feed pipe, said backpressure pump being provided in an auxiliary backpressure pipe branching from said feed pipe, said pressure relief valve being provided in a discharge pipe branching from said feed pipe or said auxiliary backpressure pipe, and a backpressure being supplied to said sterilizer by means of said feeding device, and one of said aseptic tank, said backpressure pump and said pressure relief valve.

In addition, the invention provides a sterilizing apparatus comprising at least a sterilizer, a feeding device for feeding materials into said sterilizer, an aseptic tank capable of controlling air pressure which is provided to the rear of said sterilizer, a backpressure pump and a cooler capable of passing solid particles, said aseptic tank being connected to said sterilizer by means of a feed pipe, said backpressure pump and said cooler being provided in an auxiliary backpressure pipe branching from said feed pipe, and a backpressure being supplied to said sterilizer by a combination of said feeding device and one of said aseptic tank and said backpressure pump.

BRIEF DESCRIPTION OF THE DRAWINGS

The drawings illustrate embodiments of the sterilization apparatuses of the invention.

DETAILED DESCRIPTION OF THE PREFERRED EMBODIMENTS

The invention will be described in detail with reference to the drawings.

Figure 1:
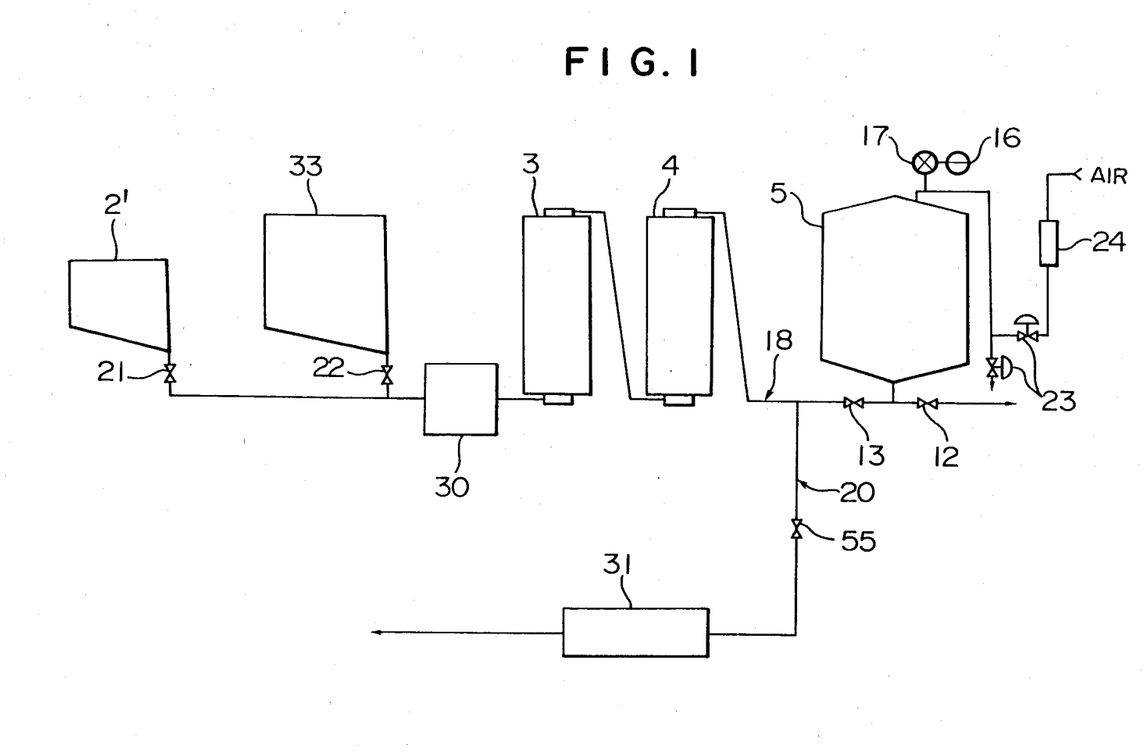
FIG. 1 is a flow diagram of a sterilization apparatus wherein a backpressure is supplied by a feeding device and a backpressure device.

FIG. 1 is a flow diagram showing a preferred embodiment of the sterilizing apparatus of the invention.

In the apparatus, a water tank 2', a products tank 33, a feeding device 30 for feeding materials into a sterilizer 3, the sterilizer 3, a cooler 4 and a backpressure tank 5 capable of controlling air pressure are provided in such order in a feed pipe 18. Also, a backpressure device 31 for supplying a backpressure to the sterilizer 3 and capable of passing solid particles is provided in an auxiliary backpressure pipe 20 branching from the feed pipe 18 at a section behind the sterilizer 3.

The feeding device 30 forces the materials to the sterilizer 3 and can pass solid particles therethrough. The feeding device 30 includes, for example, a feeding pump 32 (in FIG. 3), a feed tank 1 (in FIG. 2 and FIG. 4) capable of controlling air pressure, etc. If the feed tank 1 is used, a products tank 33 and the feeding pump 32 may be eliminated. The feeding pump 32 should have a discharge pressure greater than the backpressure, and includes, for example, a monoscrew type pump, a tubing type pump, a rotary pump, etc. with relatively high quantitative properties. The feed tank 1 functions to control the flow rate of the materials fed into the sterilizer 3 at a predetermined flow rate by use of the air pressure. For example, control of the flow rate is carried out as follows: The flow rate of the materials forced into the sterilizer 3 is detected by means of a flow meter 36 (refer to FIG. 2) provided behind the feed tank 1 and instructions are sent to a flow rate controller 37 (refer to FIG. 2) which operates a pressure relief valve 23 (refer to FIG. 2). The flow meter 36 should be a flow meter capable of passing solid particles. The air pressure in the feed tank 1 may also be controlled by means of an air regulator, etc.

The sterilizer 3 includes, for example, plate type, tube type, scraper type (a scraped surface type) or any of various other types of heat exchangers, a steam injection, etc., which can pass solid particles and are capable of conducting heat treatment at a high temperature in a short time. If required, these heat exchangers and heaters may be used in series. If the materials are of high viscosity, a scrape surface heat exchanger is particularly useful.

The cooler 4 cools the sterilized materials to a prescribed temperature, and must pass solid particles therethrough. For example, plate type, tube type, scraper type or any of various other types of heat exchangers can be used as the cooler 4.

The backpressure tank 5 supplies a backpressure to the sterilizer 3, and at the same time, collects the sterilized product. As in the feed tank 1, the backpressure tank 5 is provided with, for example, a pressure sensor 17 and a pressure controller 16, and functions to control the pressure inside the tank to a constant level by use of air (otherwise, it is possible to use an air regulator for controlling the pressure inside the tank). Also, the backpressure tank 5 and the feed tank 1 may be provided with an agitation function, if required.

The backpressure means 31 supplies a backpressure to the sterilizer 3 and is capable of passing solid particles. For example, a pump (which may be a pump capable of supplying a stable backpressure, for example, at a temperature ranging from normal temperature to 150° C.), a tank, a pressure device, etc. capable of controlling the air pressure may be used as the backpressure device 31. If an ordinary pump to which a backpressure cannot be supplied at a high temperature and a high pressure is used, a cooler or special piping should desirably be provided in the sterilization apparatus so as not to subject the pump to high temperature and high pressure. A detailed example will be described later.

Next, actual operation of the sterilization apparatus will be described.

In general, the sterilization apparatus is operated according to the following steps. First, the apparatus is sterilized with hot water under a pressure 3.0-4.5 kg/cm$^2$, for example, at 130°-150° C. for 30 min. or more so as to assure the sterility of the whole apparatus before starting operation (sterilization of apparatus). Second, the cooler is operated in the above sterilized condition (operation with water). Third, the change-over from operation with water to operation with the product is begun. Fourth, the change-over from operation with water to operation with the product is completed (operation with products).

In the sterilization apparatus shown in FIG. 1, a switch valve 21 is made open at the 1st stage of sterilization of the apparatus. Water fed from the water tank 2' into the apparatus is sent into the sterilizer 3 by means of the feeding device 30, and is heated usually to 130°-150° C. At this stage, a switch valve 55 is opened, and switch valves 13 and 22 are closed. The cooler 4 is not in operation. Therefore, heated water is discharged out of the apparatus through the feed pipe 18, the auxiliary backpressure pipe 20 and the backpressure device 31. At this step, a constant backpressure is supplied by the backpressure device 31 to the hot water passages in the apparatus. Thus, water is completely sterilized in the sterilizer 3, and at the same time, the feed pipe 18 and the auxiliary backpressure pipe 20 through which the product will pass are sterilized with heated water.

At this stage, hot water discharged through the auxiliary backpressure pipe 20 sometimes exceeds 100° C. If this is discharged out of the apparatus without cooling, it vigorously boils simultaneously with discharge. Therefore, it is desirable to provide a cooler 28 (shown in FIG. 2 and FIG. 3) at an appropriate position in the auxiliary backpressure pipe 20. Plate type, tubing type, scraper type or any of various other types of heat exchangers may be used as the cooler 28.

The backpressure tank 5 is independently sterilized with saturated steam, etc. The apparatus should be assembled so as to achieve predetermined sterilization conditions and to avoid stay of drain or contamination with air at the sterilization of apparatus.

Operation with water is carried out in a manner similar to that for the sterilization of the apparatus, except that the cooler 4 is operated. For example, cooling is carried out to lower the water temperature to about 50° C. In this step, water is continuously discharged out of the apparatus. Also, a constant backpressure is supplied to the sterilizer 3 by means of the backpressure device 31 so as to sterilize the water and to maintain the sterility of the feed pipe 18.

After operation with water, the switch valve 21 is closed and the switch valve 22 is opened to feed the product in the products tank 33 into the apparatus. A mixture of water and the product is discharged through the auxiliary backpressure pipe 20 in a manner similar to that in operation with water. In this step, a constant backpressure is supplied to the sterilizer 3 by the backpressure device 31. In changing over from water to the product, the internal pressure of apparatus is instable. However, since the internal pressure of an auxiliary backpressure tank 7 is controlled to a predetermined pressure by the air pressure, the internal pressure of apparatus does not fall lower than the predetermined pressure.

When the apparatus is sufficiently sterilized and the product alone flows in the apparatus, the switch valve 55 is closed and the switch valve 13 is opened to connect to the backpressure tank 5 the product which has been heated and cooled. The product is successively sent into the sterilizer 3 at a constant flow rate by means of the feeding device 30. At the same time, the product is forced back to the feeding device 30 side by the air pressure in the backpressure tank 5. Thus, a stable backpressure is always supplied to the sterilizer 3 so as to sterilize the products in constantly high temperature conditions.

The backpressure supplied to the inside of the apparatus should desirably be about 0.5 kg/cm$^2$ or more higher than the saturated steam pressure at the highest sterilization temperature established. If the backpressure is set at a value lower than the saturated stem pressure, lowering of pressure around the site of boiling, and causes the materials boil in the sterilizer 3. This induces boiling by chain reaction around the site of boiling.

If completely sterile products are desired, air injected into the backpressure tank 5 should be sterile air passed through, for example, an air filter (not shown in the drawings), etc.

It is difficult to carry out switching of the switch valves 13 and 55 at the same time in the change-over operation to the backpressure tank 5. However, a counter flow from the auxiliary backpressure pipe 20 to the backpressure tank 5 is prevented and impairment of sterility is prevented if the pressure inside the backpressure tank 5 is controlled to be slightly higher than the pressure supplied by the backpressure device 31. The pressure difference between the internal pressure of the backpressure tank 5 and the pressure by the backpressure device 31 should preferably be 0–0.2 kg/cm$^2$. Consequently, it is not required to sterilize the auxiliary backpressure pipe 20 including the backpressure device 31. In this respect, the process is not complex.

If the feeding device 30 is a tank capable of controlling the air pressure, the product is sent into the sterilizer 3 by the air pressure. Even if the product contains solid particles, the solid particles are not broken up.

Since the backpressure is controlled by use of air, the backpressure is extremely stable irrespective of changes in flow rate of the materials and can be controlled accurately and rapidly. In addition, since there are no small holes or narrow gaps in the apparatus, no clogging occurs even in the treatment of a highly viscous product or a product containing solid particles.

The sterilized product is gradually stored in the backpressure tank 5. When the backpressure tank becomes full with the sterilized product, the switch valve 13 is closed and a switch valve 12 is opened to feed the sterilized product to the next processes such as filling and packaging. The backpressure tank 5 should be made of a pressure-resisting material (for example, a material capable of resisting a high pressure of about 1 kg/cm$^2$ or more greater than the backpressure) but its shape is not critical.

Another embodiment of the sterilization apparatus of the invention will be described below.

Figure 2:
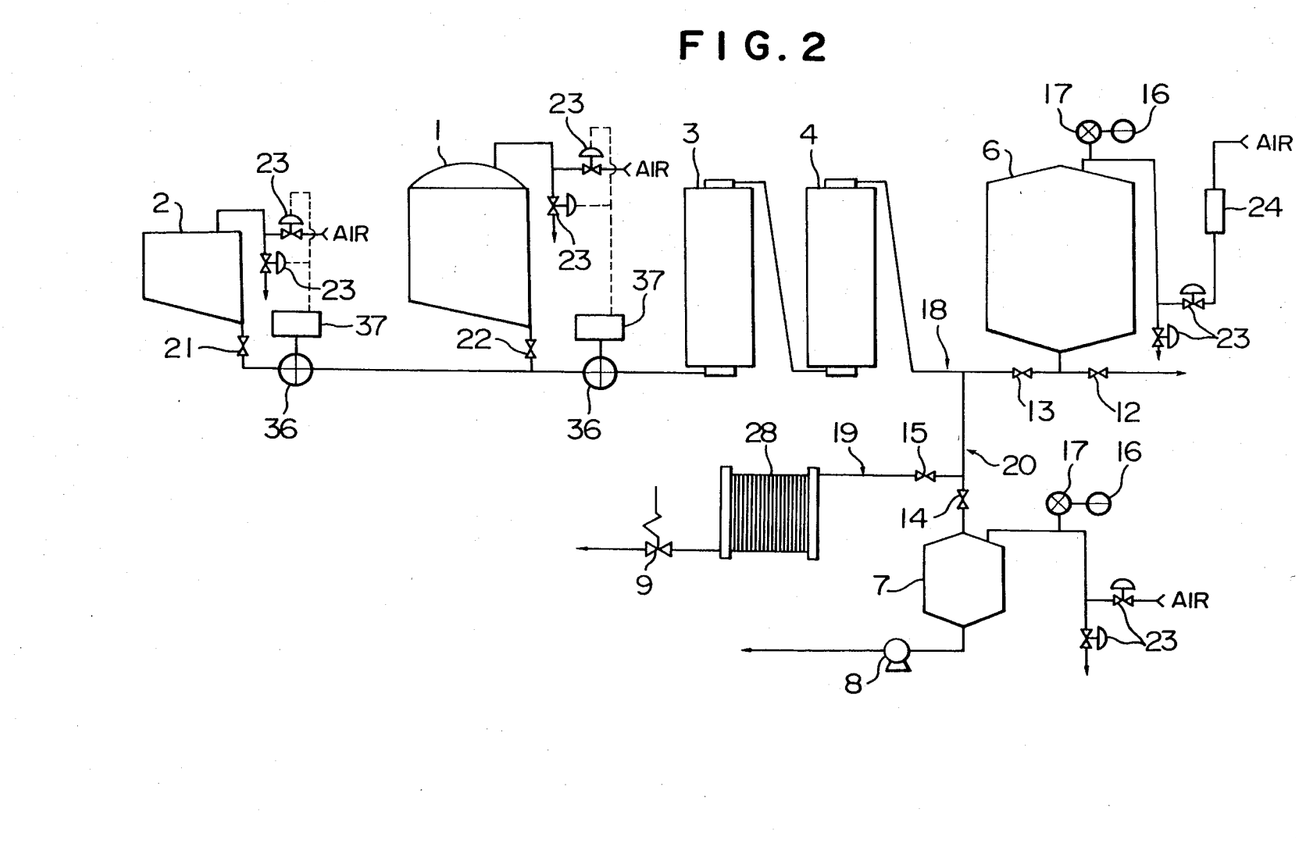
FIG. 2 is a flow diagram of a sterilization apparatus wherein a backpressure is supplied by means of a feed tank and an aseptic tank, or the feed tank and an auxiliary backpressure tank, or the feed tank and a pressure relief valve.

In the sterilizing apparatus of the invention in FIG. 2, the feed tank 1, the sterilizer 3 and the cooler 4 connected to each other by means of the feed pipe 18 are the same as those in FIG. 1. A water tank 2 is similar to the feed tank 1. It is possible to use a combination of the water tank 2', the products tank 33 and the feeding pump 32 as a feeding device in place of a combination of the water tank 2 and the feed tank 1. An aseptic tank 6 and an auxiliary backpressure tank 7 correspond to the backpressure tank 5 in FIG. 1. The aseptic tank 6 and the auxiliary backpressure tank 7 each have the pressure sensor 17 and the pressure controller 16, and are capable of controlling their internal pressures. The aseptic tank in the specification and claims is a backpressure tank in which the pressure inside the tank is controlled with sterile air.

A discharging pump 8 should preferably be a mono type pump, a tubing type pump, a rotary pump, etc. which can minimize air leakage from the apparatus. In the sterilization apparatus of the invention, it is also possible to use a valve such as a diaphragm valve, a ball valve, etc. in place of the discharging pump 8.

In the sterilization apparatus, the auxiliary backpressure pipe 20 is branched from the feed pipe 18, which extends from the feed tank 1 to the aseptic tank 6, at a section behind the sterilizer 3. A discharge pipe 19 is branched from the feed pipe 18 at the same section or from the auxiliary backpressure pipe 20 at a section before the auxiliary backpressure tank 7.

The sterilization apparatus is actually operated as follows.

In the first step of sterilization of the apparatus, the switch valve 21 is opened, and water fed from the water tank 2 by air pressure is sent into the sterilizer 3 and heated, usually at 130°–150° C. In this step, a switch valve 15 is opened and the stitch valves 13, 14 and 22 are closed. The cooler 4 is not in operation. Therefore, heated water is discharged through the feed pipe 18, the auxiliary backpressure pipe 20, a discharge pipe 19 and a pressure relief valve 9 in the order mentioned. In this step, a constant backpressure is supplied to the apparatus by means of the pressure relief valve 9. So, water is sufficiently sterilized in the sterilizer 3, and the feed pipe 18 and the auxiliary backpressure pipe 20 before the switch valve 14 are sterilized with heated water.

It is also preferable to provide a cooler 28 at an appropriate site in the discharge pipe 19 or the auxiliary backpressure pipe 20 in a manner similar to that in FIG. 1. The aseptic tank 1 is independently sterilized by saturated steam, etc.

Operation with water is carried out in a manner similar to the sterilization operation of apparatus described above, except that the cooler 4 is operated at the initial stage. When the water temperature after cooling is lowered to, for example, about 50° C., the switch valve 14 is opened and a switch valve 15 is closed. Thus, water fed from the water tank 2 is sent to the auxiliary backpressure tank 7 through the auxiliary backpressure pipe 20 after heating and cooling. Water in the auxiliary backpressure tank 7 is discharged by means of the discharging pump 8. In this step, a stable backpressure is supplied to the sterilizer by the air pressure in the auxiliary backpressure tank 7. Thus, the water is sufficiently sterilized and the sterility of the feed pipe 18 is maintained.

In switching the switch valves 14 and 15, it is desirable to change the valves over to the auxiliary backpressure tank 7 side after adjustment of the pressure by the pressure relief valve 9 and the internal pressure of the auxiliary backpressure tank 7 to almost the same level. This is for the purpose of minimizing the change in the flow rate of the materials an the change in the backpressure at the time of change-over operation. As will be described later, change-over of water to the product should desirably be carried out after confirmation of the fact that the flow rate of the materials and the backpressure have stabilized.

After completion of operation with water, the switch valve 21 is closed and the switch valve 22 is opened so as to feed the product from the feed tank 1 into the apparatus. A mixture of water and the product is discharged through the auxiliary backpressure pipe 20 in a manner similar to that in operation with water.

Thus, even if the product contains solid particles or is highly viscous, the mixture of water and the product may continuously be discharged out of the apparatus thanks to installation of the auxiliary backpressure tank 7. In addition, there is no risk of accumulation of particles and blockage. Water or the mixture of water and the product sent into the auxiliary backpressure tank 7 flows continuously from the auxiliary backpressure tank 7 by means of the drawing pump 8.

Discharging of the treated materials should desirably start after the mixture enters the auxiliary backpressure tank 7 so that the internal pressure of the auxiliary backpressure tank will not decrease. Also, the amount of the treated materials discharged from the auxiliary backpressure tank 7 should be slightly greater than the amount of the materials fed into the said tank so as to prevent overflow of the materials from the said tank even when an increase in flow rate occurs due to fluctuations. However, the amount of discharging should be controlled to such an extent that the internal pressure of the auxiliary backpressure tank 7 does not decrease.

According to the above procedures, the mixture of water and the product can be continuously discharged. At the same time, a constant backpressure is supplied to the sterilizer 3.

If a valve is used in place of the discharging pump 8, opening and shutting of the valve are carried out under predetermined conditions so as to discharge the treated materials by use of the air pressure in the auxiliary backpressure tank 7.

Since the treated materials are continuously discharged from the auxiliary backpressure tank 7 by means of the discharging pump 8 or the valve, the capacity of the auxiliary backpressure tank 7 may be minimized. Thus, the auxiliary backpressure tank section in the apparatus may be made compact in size.

Also, it is not required to use a special pump which can function even at a high temperature and a high pressure as the discharging pump, because water heated to a high temperature in the sterilizer 3 does not pass through the discharging pump 8 in the sterilization apparatus. If the discharge pipe 19 cannot be installed, a special pump is used as the discharging pump 8 so as to discharge hot water during the sterilization of apparatus through the auxiliary backpressure pipe 20.

Also, a cooler such as a scraped surface type heat exchanger, etc. which may pass solid particles-containing materials or highly viscous materials through may be provided between the switch valve 14 in the auxiliary backpressure pipe 20 and the auxiliary backpressure tank 7 in the sterilization apparatus of the invention. In this system, heated water used during the sterilization of the apparatus is cooled in the cooler, and so the discharging pump 8 is not subjected to a high temperature and high pressure condition. Therefore, even if the discharging pipe 19 is not provided, the treated materials can, during the sterilization of apparatus, the operation with water and the change-over operation, be discharged through the auxiliary backpressure pipe 20 only.

When the apparatus is sufficiently sterilized and the product alone flows through the apparatus, the switch valve 14 is closed and the switch valve 13 is opened so as to collect the sterilized products into the sterile tank 6. In the change-over operation of the switch valves 13 and 14, the internal pressure of the aseptic tank 6 is controlled to be slightly (e.g., 0.2 kg/cm$^2$) higher than the internal pressure of the auxiliary backpressure tank 7 so as to prevent counterflow of the materials from the auxiliary backpressure tank 7 to the aseptic tank 6. Thus, the sterility of the apparatus can be maintained. Therefore, it is not necessary to substantially sterilize the auxiliary backpressure pipe 20 at a section behind the switch valve 14. This makes the process simple. Also, a constant backpressure is supplied to the sterilizer by the air pressure controlled in the aseptic tank 6, and the materials are sufficiently sterilized at a high temperature.

In the apparatus where the feed tank 1 is provided to feed the products by air pressure, solid particles contained in the products are not broken up and are sufficiently protected, and at the same time, control of backpressure can be accurately carried out.

Finally, the switch valve 13 is closed and the switch valve 12 is opened so as to send the treated products collected in the aseptic tank 6 to the next process such as filling and packaging.

Still another embodiment of the sterilization apparatus of the invention will be described below.

Figure 3:
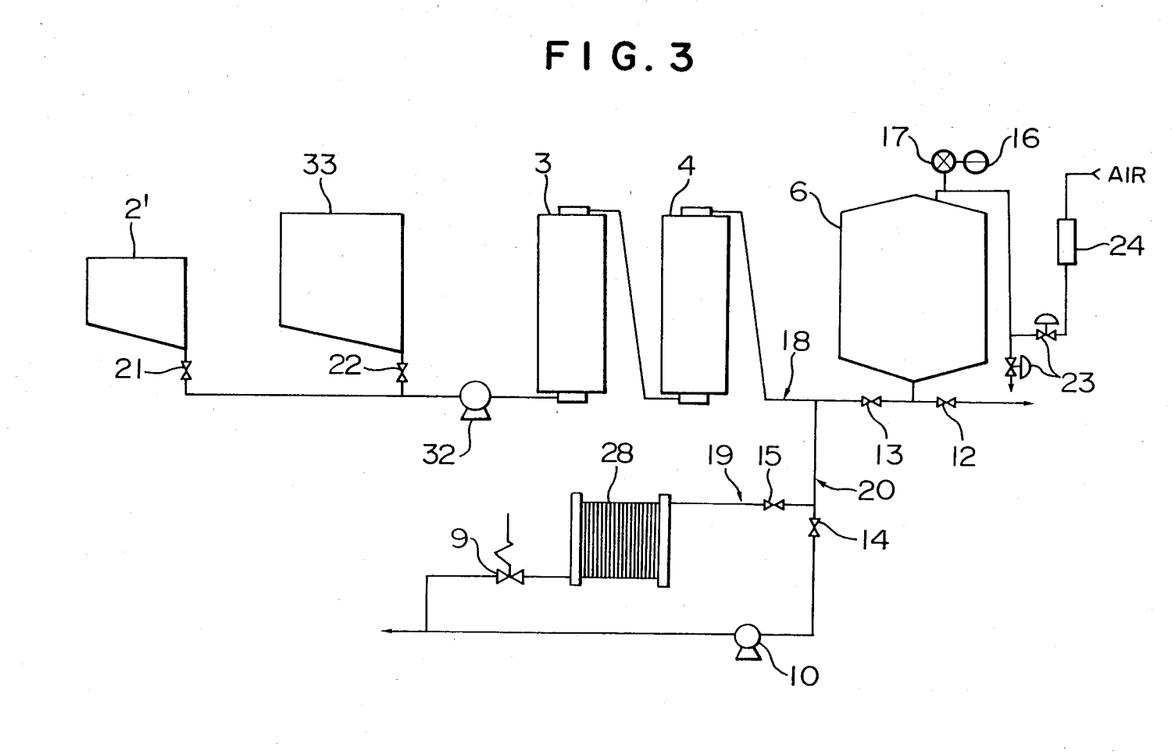
FIG. 3 is a flow diagram of a sterilization apparatus wherein a backpressure is supplied by means of a feed pump and an aseptic tank, or the feed pump and a backpressure pump, or the feed pump and a pressure relief valve.

In the sterilization apparatus of the invention shown in FIG. 3, the device connected by means of the feed pipe 18 are similar to those in FIG. 1 and FIG. 2. A mono type pump, a tubing type pump, a rotary pump, etc. having relatively high positive displacement performance should preferably be used as the backpressure pump 10. The cooler 28 and the pressure relief valve 9 are similar to those in FIG. 2. Also, a combination of the feed tank 1 and the water tank 2 may be used in place of a combination of the water tank 2', the products tank 33 and the feeding pump 32.

In the sterilization apparatus, the auxiliary backpressure pipe 20 branches from the feed pipe 18, and the discharge pipe 19 branches from the feed pipe 18 or the auxiliary backpressure pipe 20 in a manner similar to that in FIG. 2.

The sterilization apparatus is actually operated as follows.

At the first stage of sterilization of the apparatus, water fed from the water tank 2' into the apparatus by means of the feeding pump 32 is sent into the sterilizer for heating (usually to 130°–150° C.). Heated water is sent into the cooler 4 (not in operation), the feed pipe 18, the auxiliary backpressure pipe 20 and the discharge pipe 19 in the order mentioned. Heated water is cooled in the cooler 28 to, for example, 100° C. or less and is discharged out of the apparatus through the pressure relief valve 9. At this time, a constant backpressure is supplied to the sterilizer 3 by means of the pressure relief valve 9 so as to heat the water under stable conditions. The feed pipe 18 and the auxiliary backpressure pipe 20 before the switch valve 14 through which the product passes are sufficiently sterilized with heated water. At this time, the switch valves 13, 14 and 22 are closed, and the switch valve 15 is opened.

At the second stage of operation with water, the cooler 4 starts operation. When the temperature of the water passed through the cooler 4 reaches as low as 50° C. or less, for example, the operation of the cooler 28 is stopped. Then, the switch valve 15 is closed and the switch valve 14 is opened. The change-over operation of the switch valves 14 and 15 is similar to that in FIG. 2.

According to the above procedures, the backpressure pump 10 provided in the auxiliary backpressure pipe 20 is not placed at the extremely high temperature, and a constant backpressure may be supplied to the sterilizer 3 by means of the backpressure pump 10. It is not required to use an aseptic pump which is capable of enduring a high temperature and a high pressure as the backpressure pump 10, since the product does not pass through the backpressure pump 10 and the invasion of bacteria from the backpressure pump 10 into the product passages is prevented by establishment of the internal pressure of the sterile tank 6 at a level slightly higher than the backpressure supplied by the backpressure pump 10.

After stabilization of operation with water, the switch valve 21 is closed and the switch valve 22 is made open so as to feed the products from the products tank 33. At the time, a constant backpressure is supplied to the sterilizer 3 by means of the backpressure pump 10 in a manner similar to the above, and a mixture of water and the products is discharged through the auxiliary backpressure pipe 20 without destruction of the sterility of the apparatus.

When the mixture is completely changed over to the products, the switch valve 14 is closed and the switch valve 13 is made open so as to collect the products into the aseptic tank 6. The aseptic tank 6 is similar to that used in FIG. 2. At the actual operation with the products, a constant backpressure is always supplied to the sterilizer 3 by use of the air pressure controlled in the aseptic tank 6.

Finally, the switch valve 13 is closed and the switch valve 12 is opened so as to deliver the product collected in the aseptic tank 6 to the next process such as filling and packaging.

Still another embodiment will be described below.

Figure 4:
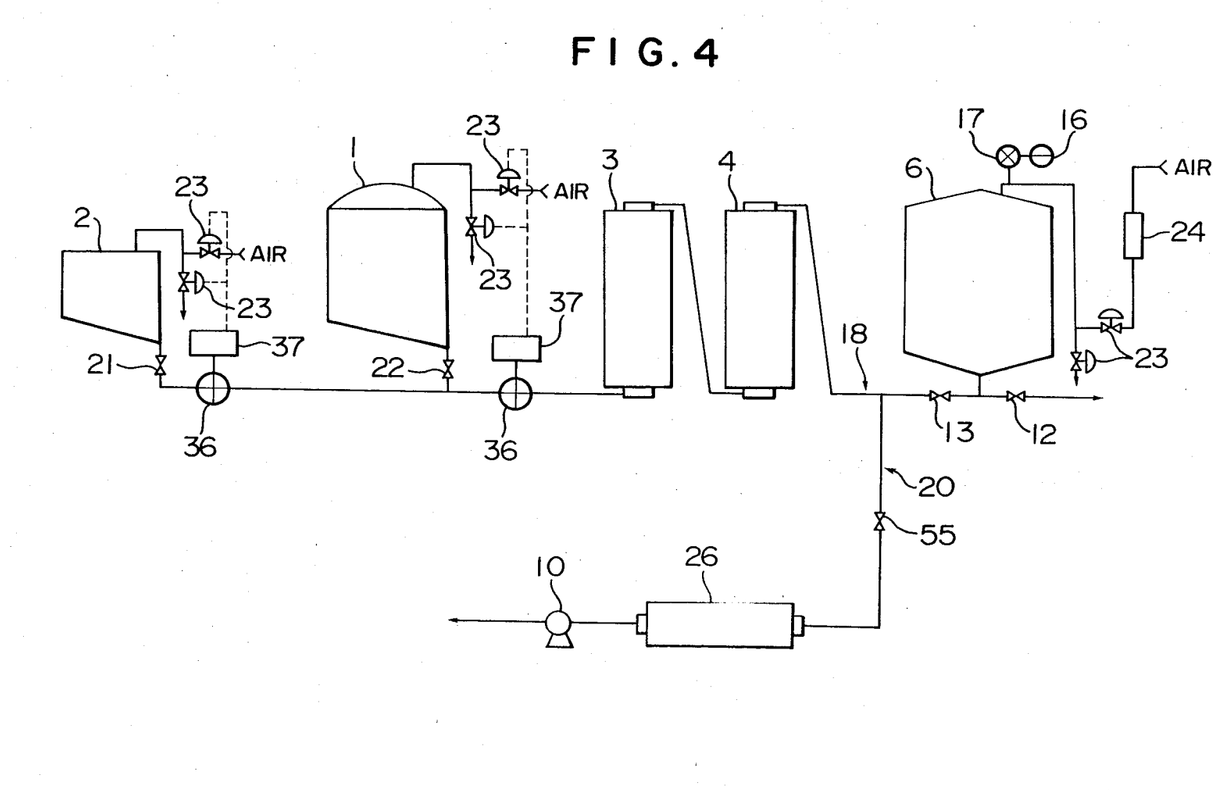
FIG. 4 is a flow diagram showing a sterilization apparatus wherein a backpressure is supplied by means of a feed tank and an aseptic tank, or the feed tank and a backpressure pump.

In the sterilization apparatus of the invention shown in FIG. 4, the devices connected by the feed pipe 18 are similar to those in FIG. 1, FIG. 2 and FIG. 3. Tube type, scraper type or any of various other types of heat exchangers which can pass solid particles may be used as a cooler 26. The backpressure pump 10 is similar to that in FIG. 3. Also, a combination of the water tank 2', the products tank 33 and the discharging pump 32 may be used in place of a combination of the feed tank 1 and the water tank 2.

In the sterilization apparatus, the auxiliary backpressure pipe 20 branches from the feed pipe 18, which extends from the feed tank 1 to the aseptic tank 6, at a section behind the sterilizer 3.

The sterilization apparatus is operated as follows.

At the first stage of sterilization of the apparatus, water fed from the water tank 2 into the apparatus is heated in the sterilizer 3. Heated water is sent to the cooler 26 through the cooler 4 (not in operation), the feed pipe 18 and the auxiliary backpressure pipe 20 in the order mentioned. Heated water cooled in the cooler 26 to a temperature below, for example, 50° C. is discharged out of the apparatus through the backpressure pump 10. The cooler 26 is capable of passing solid particles, and is provided in the auxiliary backpressure pipe 20 before the backpressure pump 10 and behind the switch valve 55. Thus, the backpressure pump 10 is not subjected to a high temperature during the sterilization of the apparatus because of the operation of the cooler 26. A constant backpressure is supplied by means of the backpressure pump 10 in the apparatus, and the water is always heated in a constant condition. The feed pipe 18 and the auxiliary backpressure pipe 20 before the switch valve 55 through which the product substantially passes are sufficiently sterilized. At this time, the switch valves 22 and 13 are closed, and the switch valve 55 is opened. In the sterilization apparatus, the backpressure pump 10 is not placed at a high temperature because of the operation of the cooler 26. Also, invasion of bacteria from the backpressure pump 10 into the product passage may be prevented in a manner similar to that in FIG. 3 by establishment of the internal pressure of the aseptic tank 6 at a level slightly higher than the backpressure supplied by the backpressure pump 10 during change-over operation of the switch valve 13 and 55. Therefore, it is not required to use a pump of sterile specifications and durable against high temperatures and pressures.

In the second stage of operation with water, the cooler 4 starts operation. When the temperature of water passing through the cooler 4 falls to, for example, 50° C. or less, the operation of the cooler 26 is stopped. Therefore, the backpressure pump 10 is not subjected to extremely high temperatures. At the same time, a constant backpressure can be supplied to the sterilizer 3 by means of the backpressure pump 10. The conditions of the switch valves are similar to those for the sterilization of the apparatus.

After stabilization of operation with water, the switch valve 21 in the water tank 2 is closed, and the switch valve 22 is opened so as to feed the product from the feed tank 1 for product operation. Since the product is fed by air pressure at the time, solid particles, etc. contained in the product are not broken up. Also, a constant backpressure is supplied to the sterilizer 3 by means of the backpressure pump 10 in a manner similar to the above, and a mixture of water and the product is discharged through the auxiliary backpressure pipe 20 without disturbing the sterility inside the apparatus.

When the mixture has been completely changed over to the product, the switch valve 55 is closed, and the switch valve 13 is opened so as to collect the product into the aseptic tank 6. The aseptic tank 6 is a pressurized tank which is capable of constantly controlling its internal pressure by use of the pressured air (sterile air). Thus, a stable backpressure is always supplied to the sterilizer 3 by the air pressure controlled in the aseptic tank even in product operation.

Finally, the switch valve 13 is closed and the switch valve 12 is opened to feed the product collected in the aseptic tank 6 to the next process such as filling and packaging, etc.

According to the sterilization apparatuses shown in FIG. 3 and FIG. 4, the backpressure pump is not subjected to extremely high temperature because of the operation of the cooler or in a route because of the installation of the backpressure pump independent from the piping for passing the product. Also, a constant backpressure can be supplied to the sterilizer. In addition, the materials other than the product can be continuously discharged out of the apparatus, and the product alone can be collected into the aseptic tank under application of a constant and stable backpressure inside the apparatus while keeping the apparatus sterile.

According to the sterilization apparatus of the invention, it is possible to sterilize the materials at a constant high temperature under application of a constant backpressure to the inside of the apparatus, and the control of the backpressure can simply and accurately be carried out. Also, hot water during sterilization of apparatus, water during operation with water, and a mixture of water and the product during change-over oberation can be continuously discharged out of the apparatus and the product alone can be collected under application of a constant backpressure to the inside the apparatus, with the sterility of the product passage maintained.

According to the sterilization apparatus of the invention, there is no risk of accumulation of particles and blockage and solid particles in the product are not broken up even in the treatment of highly viscous materials or solid particles-containing materials. Thus, the sterilization apparatus of the invention is markedly effective in sterilizing liquid food containing solid particles or highly viscous food and medicines, and in processing these products by sterile collection.

EXAMPLE

An embodiment of the sterilization apparatus of the invention and a process of sterilizing soup containing kernels of corn by use of the apparatus will be described.

Figure 5:
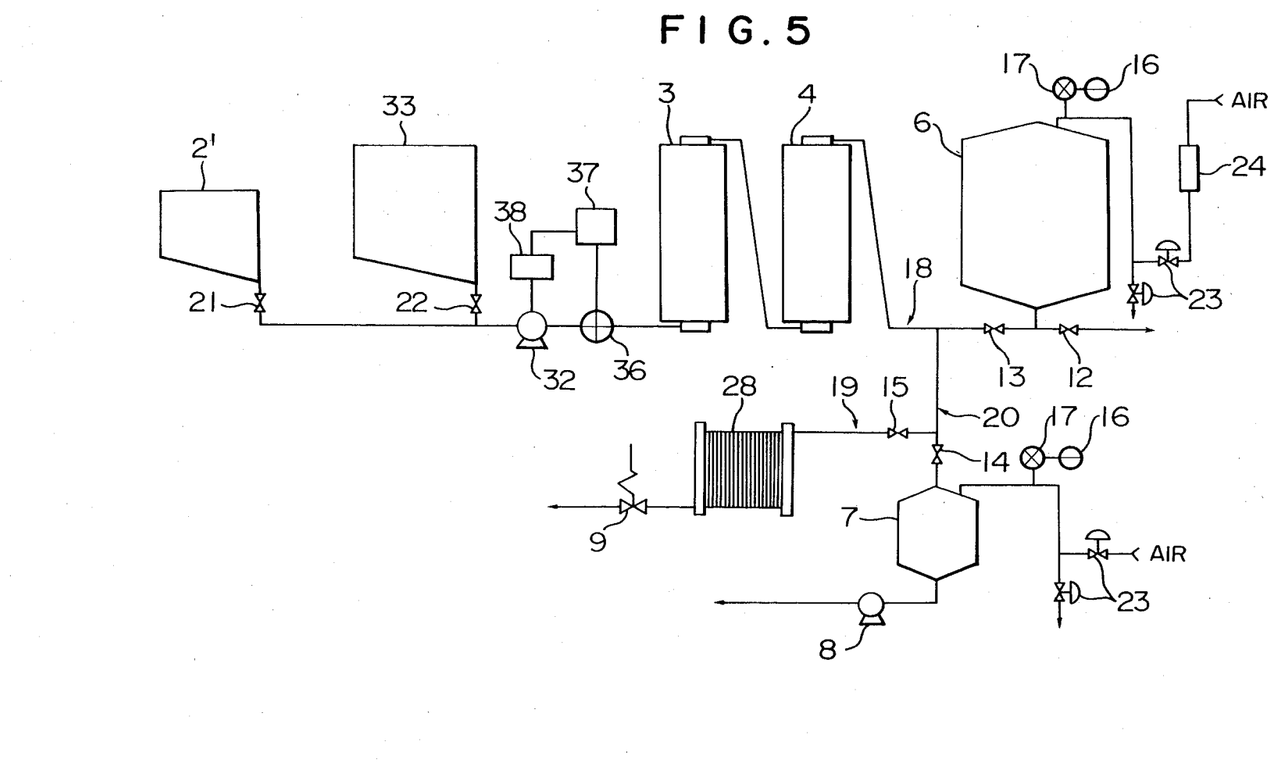
FIG. 5 is a flow diagram showing a sterilization apparatus employed in an example.

An embodiment of the sterilization apparatus is shown in FIG. 5. A stainless steel hopper tank was used for the water tank 2' and the products tank 33. Also, a monotype pump with a discharge capacity of about 1–6 t/hr was used for the feeding pump 32. The flow meter 36 was a micromotion flow meter capable of passing solid particles. The flow meter 36 detects the flow rate of materials fed into the sterilizer 3. (A magnetic flow meter, an ultrasonic flow meter, etc. may be used instead.) The flow rate controller 37 receives the detected value in the flow meter 36, and sends an instruction to an inverter 38 so as to change the rotation speed of the feeding pump 32. A scraped surface heat exchanger was used for the sterilizers 3 and 4. The aseptic tank 6 was made of stainless steel, with a pressure resistance of 3.0 kg/cm$^2$ and a capacity of 5 t. The aseptic tank 6 was equipped with the pressure sensor 17 and the pressure controller 16, and was capable of controlling its internal pressure to a constant level by use of sterile air fed through a sterile filter 24. The above units were connected in the order mentioned by means of a stainless steel feed pipe 18.

The auxiliary backpressure tank 7 was made of stainless steel and had a pressure resistance of 3–5 kg/cm$^2$ and a capacity of 5–10 t. As in the aseptic tank 6, the auxiliary backpressure tank 7 was equipped with the pressure sensor 17 and the pressure controller 16 and was capable of controlling its internal pressure by air. A mono pump with a discharge capacity of 1–6 t/hr was used for the discharging pump 8. The auxiliary backpressure tank 7 and the drawing pump 8 were connected to each other by means of the auxiliary backpressure pipe 20 branching from the feed pipe 18 at a section behind the cooler 4.

A plate type heat exchanger was used for the cooler 28. The cooler 28 and the pressure relief valve 9 were connected to each other by means of the drain pipe 19 branching from the auxiliary backpressure pipe 20 at a section before the switch valve 14.

An example of the sterilizing treatment of the corn soup by use of the sterilization apparatus is described below.

1. Sterilization of apparatus:

First, the switch valve 15 was opened, and the switch valves 13, 14 and 22 were closed. Then, water was fed from the water tank 2 into the apparatus, and was sent into the sterilizer 3 at a flow rate of about 1,400–1,600 l/hr by means of the feeding pump 32. Control of the flow rate was carried out as follows. If the flow rate exceeded the set-up flow rate, the flow meter 36 delivered a signal to the flow rate controller 37. The flow rate controller sent an instruction to the inverter 38 so as to increase the rotation speed of the feeding pump 32 to a predetermined speed. Then, water was fed at the set-up flow rate by means of the feeding pump 32.

Water fed by means of the feeding pump 32 was heated to about 140° C. in the sterilizer 3. This heated water was passed through the feed pipe 18, the auxiliary backpressure pump 20 and the discharge pipe 19, and was discharged through the pressure relief valve 9. At this time, a backpressure of 4.0 kg/cm$^2$ was supplied inside the apparatus by means of the pressure relief valve 19.

The above sterilization of the apparatus was carried out for about 30 min. after confirmation of the fact that the temperature of hot water at a section before the pressure relief valve 9 had reached 130° C.

Separately from the above route, saturated steam of about 2.0–3.0 kg/cm$^2$ was injected into the aseptic tank 6 so as to carry out sterilization inside the tank.

2. Operation with water:

The cooler 4 was operated so as to cool heated water to about 50° C. or less. When the temperature of the water passed through the cooler 4 had decreased to about 50° C. or less, the set-up temperature for the sterilizer 3 was gradually decreased from 140° C. (sterilization temperature for water) to 134°-136° C. sterilization temperature for the product). After confirmation of the fact that the temperature at the sterilizer 3 was stabilized at 134-136° C., the backpressure supplied by means of the pressure relief valve 9 was decreased from 4.0 kg/cm$^2$ to 2.7-2.8 kg/cm$^2$. Also, the internal pressure of the auxiliary backpressure tank 7 was adjusted to 2.7-2.8 kg/cm$^2$. When the flow rate was stabilized under such conditions, the switch valve 14 was opened and the switch valve 15 was closed so as to feed heated water after cooling to the auxiliary backpressure tank 7 through the auxiliary backpressure pipe 20. Water stored in the auxiliary backpressure tank 7 was discharged by means of the discharging pump 8. The discharge flow rate of the discharging pump 8 was adjusted to 1,400-1,600 l/hr.

3. Change-over operation:

After completion of operation with water, the switch valve 21 was closed and the switch valve 22 was opened to feed the corn soup from the products tank 33 into the apparatus. A mixture of water and the soup was discharged through the auxiliary backpressure pipe 20 in a manner similar to that in operation with water. At this time, the discharge flow rate of the feeding pump 32, the temperature conditions for the sterilizer 3 and the cooler 4 were completely similar to those during operation with water. Also, the internal pressure of the auxiliary backpressure tank 7 was adjusted to 2.7-2.8 kg/cm$^2$ to supply a backpressure to the inside of the apparatus.

4. Operation with product only:

The internal pressure of the aseptic tank 6 was adjusted to 2.7-2.8 kg/cm$^2$. The materials discharged through the auxiliary backpressure pipe 20 were sampled to confirm the fact that product alone was flowing through the apparatus. Then, the switch valve 14 was closed, and the switch valve 13 was opened simultaneously with or slightly later than the change-over operation for the switch valve 14. The discharge flow rate of the feeding pump 32 and the temperature conditions for the sterilizer 3 and the cooler 4 were completely the same as those at the change-over operation. Also, the internal pressure of the aseptic tank 6 was adjusted to 2.7-2.8 kg/cm$^2$ to supply a backpressure to the inside of the apparatus. The operation with the product only was continued in the above conditions until the soup in the products tank 33 was exhausted. After the collection of the product into the aseptic tank 6, the switch valve 13 was closed.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A sterilization apparatus for continuously sterilizing materials to be treated containing solid particles therein while keeping a pressure of said apparatus unchanged, comprising:

(a) a sterilizer means for sterilizing material and for passing therethrough solid particles;

(b) a feeding device means for feeding materials to be treated to said sterilizer means;

(c) a backpressure tank means for supplying a backpressure to said sterilizer means said back pressure tank means comprising means for controlling air pressure therein;

(d) a feed pipe connecting said sterilizer means to said backpressure tank means;

(e) an auxiliary backpressure pipe branching from said feed;

(f) a backpressure device means provided in said auxiliary backpressure pipe, for supplying a backpressure to said sterilizer means so that the pressure in said sterilizer means is unchanged and for passing therefrom said solid particles; and (g) valve means positioned so as to operatively open and close communications between said sterilizer means and backpressure tank means and between said sterilizer means and said backpressure device means.

2. The sterilization apparatus as in claim 1, wherein said backpressure device means is an auxiliary backpressure tank means which includes means for controlling air pressure therein.

3. The sterilization apparatus as in claim 1, wherein said feeding device means is a feed tank means including means for controlling air pressure therein.

4. A sterilization apparatus as in claim 1, wherein said backpressure tank means is an aseptic tank means.

5. The sterilization apparatus as in claim 4, wherein said backpressure device means is an auxiliary backpressure tank means which includes means for controlling air pressure therein.

6. A sterilization apparatus for continuously sterilizing materials to be treated having solid particles therein, while keeping pressure in said apparatus unchanged, comprising:

(a) a sterilizer means for passing therethrough solid particles;

(b) a feeding device means for feeding materials to be treated into said sterilizer means;

(c) an aseptic tank means provided downstream of said sterilizer means; for supplying back pressure to said sterilizer means, whereby air pressure in said aseptic tank is controllable;

(d) a feed pipe connecting said sterilizer to said aseptic tank means;

(e) an auxiliary backpressure pipe branching from said feed pipe;

(f) an auxiliary backpressure tank means operatively connected to said auxiliary backpressure pipe;

(g) a discharge pipe branching from one of said feed pipe and said auxiliary backpressure pipe;

(h) a pressure relief valve means for controlling discharge operatively connected to said discharge pipe;

(i) a discharge pump means operatively connected to said auxiliary backpressure tank means for discharging a mixture of water and treated materials from said auxiliary backpressure tank means; and (j) valve means positioned so us to operatively open and close communications between said sterilizer means and said aseptic tank means, between said sterilizer means and said auxiliary backpressure tank means, and between said sterilizer means and said pressure relief valve means, a combination whereby said feeding device means and one of said aseptic tank means, said auxiliary backpressure means and said pressure relief valve means are arranged so as to operatively supply backpressure to said sterilizer means so that air pressure therein remains unchanged.

7. The sterilization apparatus as in claim 6, wherein said feeding device means is a feed tank means including means for controlling air pressure therein.

8. A sterization apparatus for continuously sterilizing materials to be treated having solid particles therein, while keeping pressure in said apparatus unchanged, comprising:
(a) a sterilizer means for passing therethrough solid particles;
(b) a feeding device means for feeding materials to be treated into said sterilizer means;
(c) an aseptic tank means provided downstream of said sterilizer means for supplying back pressure to said sterilizer means, said aseptic tank means comprising means for controlling the air pressure therein;
(d) a feed pipe connecting said sterilizer means to said aseptic tank means;
(e) an auxiliary backpressure pipe branching from said feed pipe;
(f) a backpressure pump means provided in said auxiliary backpressure pipe;
(g) a discharging pipe branching from one of said feed pipe and said auxiliary backpressure pipe;
(h) a pressure relief valve, means for controlling discharge provided in said discharge pipe; and
(i) valve means positioned so as to operatively open and close communications between said sterilizer means and said aseptic tank means between said sterilizer means and said backpressure pump means, and between said sterilizer means and said pressure relief valve means,
a combination whereby said feeding device means and one of said aseptic tank means, said backpressure pump means and said pressure relief valve means are arranged so as to operatively supply backpressure to said sterilizer means so that air pressure therein remains unchanged.

9. The sterilization apparatus as in claim 8, wherein said feeding device means is a feed tank means including means for controlling air pressure therein.

10. A sterilization apparatus for continuously sterilizing materials to be treated having solid particles therein, while keeping pressure in said apparatus unchanged, comprising:
(a) a sterilizer means for passing therethrough solid particles;
(b) a feeding device means for feeding materials to be treated into said sterilizer means;
(c) an aseptic tank means provided downstream of said sterilizer means for supplying back pressure to said sterilizer means, said aseptic tank means comprising means for controlling air pressure therein;
(d) a feed pipe connecting said sterilizer means to said aseptic tank means;
(e) an auxiliary backpressure pipe branching from said feed pipe;
(f) a backpressure pump means provided in said auxiliary backpressure pipe;
(g) a cooler means for cooling material and for passing therethrough said solid particles, said cooler means being provided in said auxiliary backpressure pipe; and
(h) valve means positioned so as to operatively open and close communications between said sterilizer means and said aseptic tank means and between said sterilizer means and said backpressure pump means,
a combination whereby said feeding device means and one of said aseptic tank means said backpressure pump means are arranged so as to operatively supply backpressure to said sterilizer so that air pressure therein remains unchanged.

11. The sterilization apparatus as in claim 10, wherein said feeding device means is a feed tank means.

* * * * *